(12) United States Patent
Moszner et al.

(10) Patent No.: US 9,877,898 B2
(45) Date of Patent: Jan. 30, 2018

(54) DENTAL MATERIALS BASED ON LOW-ODOUR THIOLS

(71) Applicant: Ivoclar Vivadent AG, Schaan (LI)

(72) Inventors: Norbert Moszner, Mauren (LI); Peter Burtscher, Rankweil (AT); Urs-Karl Fischer, Arbon (CH); Helmut Ritter, Wuppertal (DE); Monir Tabatabai, Düsseldorf (DE); Andreas Utterodt, Neu-Anspach (DE)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 15/113,202

(22) PCT Filed: Feb. 24, 2015

(86) PCT No.: PCT/EP2015/053847
§ 371 (c)(1),
(2) Date: Jul. 21, 2016

(87) PCT Pub. No.: WO2015/124797
PCT Pub. Date: Aug. 27, 2015

(65) Prior Publication Data
US 2017/0007505 A1 Jan. 12, 2017

(30) Foreign Application Priority Data

Feb. 24, 2014 (EP) .................................. 14156436

(51) Int. Cl.
| | | |
|---|---|---|
| *C08F 2/46* | (2006.01) | |
| *C08F 2/50* | (2006.01) | |
| *C08G 61/04* | (2006.01) | |
| *A61K 6/087* | (2006.01) | |
| *C07D 251/34* | (2006.01) | |
| *A61K 6/00* | (2006.01) | |
| *A61K 6/083* | (2006.01) | |
| *C08G 18/75* | (2006.01) | |
| *C08G 18/80* | (2006.01) | |
| *C08G 75/045* | (2016.01) | |

(52) U.S. Cl.
CPC ............ *A61K 6/087* (2013.01); *A61K 6/0052* (2013.01); *A61K 6/0073* (2013.01); *A61K 6/0091* (2013.01); *A61K 6/083* (2013.01); *C07D 251/34* (2013.01); *C08G 18/755* (2013.01); *C08G 18/8054* (2013.01); *C08G 75/045* (2013.01)

(58) Field of Classification Search
CPC .... A61K 6/087; A61K 6/0091; A61K 6/0052; A61K 6/0073; A61K 6/083; C08G 75/045; C08G 18/8054; C08G 18/755; C07D 251/34; C08L 33/10; C08L 33/26
USPC ................ 522/64, 6, 1, 189, 184, 71; 520/1
See application file for complete search history.

(56) References Cited

U.S. PATENT DOCUMENTS

| | | | |
|---|---|---|---|
| 4,266,055 A | 5/1981 | Inoue et al. | |
| 5,919,602 A | 7/1999 | Herr et al. | |
| 7,838,571 B2 | 11/2010 | Bowman et al. | |
| 8,192,673 B2 | 6/2012 | Bowman et al. | |
| 2007/0185230 A1 | 8/2007 | Bowman et al. | |
| 2009/0270528 A1 | 10/2009 | Bowman et al. | |
| 2012/0256338 A1 | 10/2012 | Bowman et al. | |
| 2012/0308532 A1* | 12/2012 | Hult .................. | A61L 27/26 424/93.7 |
| 2014/0323647 A1* | 10/2014 | Voit .................. | B29C 45/00 524/548 |
| 2015/0250687 A1* | 9/2015 | Bowman .......... | A61K 6/087 522/63 |

OTHER PUBLICATIONS

Reinelt et al, Investigations of thiol-modified phenol derivatives for the use in thiol-ene photopolymerizations, Jul. 29, 2014, Beilstein Journal of Organic Chemistry, 10, 1733-1740.*
Patel, M.P., et al., "Polymerization shrinkage of methacrylate esters," Biomaterials, vol. 8, 1987, pp. 53-56.
Cramer, N., et al., "Investigation of thiol-ene and thiol-ene-methacrylate based resins as dental restorative materials," Dental Materials, vol. 26, 2010, pp. 21-28.
Cramer, N., et al., "Properties of methacrylate-thiol-ene formulations as dental restorative materials," Dental Materials, vol. 26, 2010, pp. 799-806.
Svarovsky, S., et al., "Synthesis of gold nanoparticles bearing the Thomsen-Friedenreich disaccharide: a new multivalent presentation of an important tumor antigen," Asymmetry, vol. 16, 2005, pp. 587-598.
Snow, A. W., et al., "Conversion of Alcohols to Thiols via Tosylate Intermediates," Synthesis, No. 4, 2003, pp. 509-512.
Houk, J., et al., "Structure-Reactivity Relations for Thiol-Disulfide Interchange," J. Am. Chem. Soc., 109, 1987, pp. 6825-6836.
Chan, J.W., et al., "Nucleophile-Initiated Thiol-Michael Reactions: Effect of Organocatalyst, Thiol, and Ene," Macromolecules, 43, 2010, pp. 6381-6388.
Li, G.-Z., et al., "Investigation into thiol-(meth)acrylate Michael addition reactions using amine and phosphine catalysts," Polym. Chem., 1, 2010, pp. 1196-1224.
Mather, B.D., et al., "Michael addition reactions in macromolecular design for emerging technologies," Prog. Polym. Sci., 31, 2006, pp. 487-531.

(Continued)

*Primary Examiner* — Jessica Whiteley
(74) *Attorney, Agent, or Firm* — Ann M. Knab; Thad McMurray

(57) ABSTRACT

Dental material, which contains an ene compound with two or more C—C multiple bonds and a thiol according to general Formula (1) or an oligomer based on such a thiol,

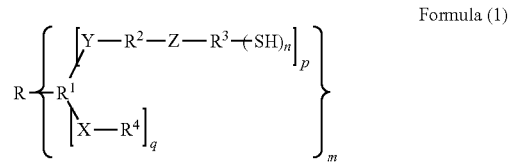

Formula (1)

wherein n, p and m are chosen such that the thiol has a total of at least 3 SH groups.

19 Claims, No Drawings

(56) References Cited

OTHER PUBLICATIONS

Li, H., et al., "The Thiol-Isocyanate Click Reaction: Facile and Quantitative Access to w-End-Functional Poly(N,N-diethylacrylamide) Synthesized by RAFT Radical Polymerization," Macromolecules, 42, 2009, pp. 6537-6542.

Abraham, M. H., et al., "Hydrogen Bonding. Part 18. Gas-Liquid Chromatographic Measurements for the Design and Selection of some Hydrogen Bond Acidic Phases Suitable for Use as Coatings on Piezoelectric Sorption Detectors," J. Chem. Soc., Perkin Trans. 2, 1991, pp. 1417-1423.

Elias, H.G., Macromolecules, vol. 1: Chemical Structure and Syntheses, Wiley-VCH, 1999, pp. 478-780.

European Committee for Standardization, EN ISO 4049, Dentistry—Polymer-based restorative materials, Filling and Restorative Materials, Fourth Edition, Oct. 1, 2009, Pages.

International Preliminary Report on Patentability of PCT/EP2015/053847, dated Aug. 30, 2016, 7 pages.

* cited by examiner

DENTAL MATERIALS BASED ON LOW-ODOUR THIOLS

CROSS-REFERENCE TO RELATED APPLICATIONS

This application is a National Stage application of International patent application PCT/EP2015/053847 filed on Feb. 24, 2015, which claims priority to European patent application No. 14156436.9 filed on Feb. 24, 2014, the disclosures of which are incorporated herein by reference in their entirety.

The present invention relates to thermally curing and/or light-curing dental materials for preparing dental cements and filling composites and for inlays, onlays, crowns, bridges or veneering materials.

Dental composites usually contain a polymerizable organic matrix and one or more fillers. In most cases a mixture of monomers, initiator components, stabilizers and pigments is used as polymerizable organic matrix, wherein mixtures of dimethacrylates are often used as resins. Such materials can be cured by thermal, redox-initiated or light-induced radical polymerization.

A substantial disadvantage of the radical polymerization of dental composites is the volume contraction caused by the polymerization shrinkage ($\Delta V_P$) of the methacrylate monomers used, which volume contraction can lead to a very disadvantageous marginal gap formation in filling composites. The polymerization shrinkage depends linearly on the concentration of the double bonds in the volume and accordingly decreases with increasing molecular weight of the monomers in the resin mixture or increasing volume fraction of fillers in the composite. Moreover, the polymerization shrinkage increases with growing functionality of the monomers and higher double bond conversion of the polymerization.

In the polymerization of monofunctional methacrylates, such as e.g. MMA ($\Delta V_P$=21.0 vol.-%), the polymerization shrinkage does not lead to the build-up of a polymerization shrinkage stress (PSS), because the reduction in the volume can be compensated for by the flow of the macromolecules formed. In the case of the cross-linking polymerization of multifunctional methacrylates, however, the formation of a three-dimensional polymer network results at the so-called gel point already within a few seconds, i.e. already at a low monomer conversion, with the result that the polymerization shrinkage can no longer be compensated for by viscous flow and a substantial PSS builds up in the material with increasing monomer conversion.

In comparison with cross-linking radical polymerization, which proceeds according to a chain growth mechanism, cross-linking polyreactions with a step growth mechanism only display a gel formation at a much higher monomer conversion. The monomer conversion at the gel point can be influenced by the functionality of the monomer units and the initial amount-of-substance ratio (cf. H.-G. Elias, Makromoleküle, Vol. 1, 6$^{th}$ edition, Weinheim etc. 1999, 478-480).

It is known that cross-linking thiol-ene polyaddition is characterized by an almost complete double bond conversion and a much lower polymerization shrinkage compared with the radical polymerization of multifunctional methacrylates. Thus the volume contraction per polymerized (meth)acrylate double bond is approx. 22-23 cm$^3$/mol, while in the case of the thiol-ene reaction the volume contraction is only 12-15 cm$^3$ per mole of converted double bond (cf. M. Patel, M. Braden, K. W. M. Davy, Biomaterials 8 (1987) 53-56). In addition, cross-linking thiol-ene polyadditions proceed according to a step growth mechanism and therefore display a significantly extended pre-gel phase compared with dimethacrylate polymerization, which additionally leads to the reduction of the PSS. Furthermore, thiol-ene systems are characterized by a low oxygen inhibition. A disadvantage of thiol-ene systems is their deteriorated mechanical properties compared with methacrylates after curing.

Cramer et al., Dent. Mater. 26 (2010), 21-28, report that materials which are comparable to bis-GMA/TEGDMA systems in respect of the modulus of elasticity and the bending strength but which have a greatly reduced PSS compared with bis-GMA/TEGDMA can be obtained by combining thiol-norbornene and thiol-allyl ether systems with the dimethacrylates bis-GMA and TEGDMA. The thiols used are said to have improved storage stability and a low odour.

According to Cramer et al., Dent. Mater. 26 (2010) 799-806, a stoichiometric ratio of thiol to ene of 3:1 in ternary methacrylate-thiol-ene systems is to be advantageous compared with a ratio of 1:1.

US 2012/0256338 A1, U.S. Pat. No. 8,192,673 B2, U.S. Pat. No. 7,838,571 B2 and US 2009/0270528 A1 disclose light-curing dental restoration materials which contain at least 10 wt.-% of a mixture of thiol monomer and ene monomer in addition to methacrylates. A preferred thiol is pentaerythritol tetramercaptopropionate (PETMP).

Despite the named advantages, thiol-ene resins have until now found no practical use in dental composites, above all because the odour of the thiol component is not acceptable for a dental use. In addition, the storage stability of conventional thiols is inadequate. Although many thiols can be prepared almost odour-free with suitable devices such as e.g. a falling film evaporator or thin film evaporator, during storage they take on an intense mercaptan odour again because of decomposition.

The object of the invention is to provide dental materials which are characterized, in comparison with materials based on dimethacrylates, by a lower residual monomer content and a reduced polymerization stress with comparable mechanical properties. In addition, they are to have olfactory properties suitable for dental purposes and a high storage stability, and not take on an unpleasant odour after longer storage. Moreover, they are to have a hydrolysis stability suitable for dental use and a low polymerization shrinkage.

The object is achieved according to the invention by dental materials which contain at least one ene compound with two or more C—C multiple bonds and at least one thiol according to general Formula (I),

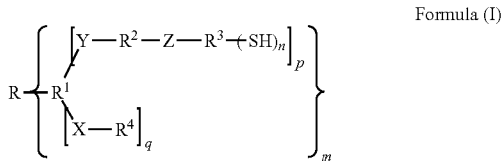

Formula (I)

in which
R is —SO$_2$—, a linear or branched aliphatic C$_{1-20}$ radical, an aromatic C$_{6-20}$ radical, a cycloaliphatic C$_{3-18}$ radical or a heterocyclic radical with 3 to 17 C atoms and 1 to 3 heteroatoms which are selected from N, O and S;
R$^1$ is absent or is a linear or branched aliphatic C$_{1-12}$ radical, an aromatic C$_{6-20}$ radical, a cycloaliphatic C$_{3-18}$ radical or a heterocyclic radical with 3 to 17 C atoms and 1 to 3 heteroatoms which are selected from N, O and S;

$R^2$ is absent or is a linear or branched aliphatic $C_{1-20}$ radical which can be interrupted by O or S, an aromatic $C_{6-10}$ radical which can be substituted by $CH_3$, $CH_2CH_3$, OH, $OCH_3$ or —O—CO—$CH_3$;

$R^3$ is absent or is a linear or branched aliphatic $C_{1-20}$ radical which can be interrupted by O or S, an aromatic $C_{6-10}$ radical which can be substituted by $CH_3$, $CH_2CH_3$, OH, $OCH_3$ or —O—CO—$CH_3$;

$R^4$ is a $C_{1-6}$ alkyl radical;

X, Y independently of each other are O, S, CO—NH, O—CO—NH or NH—CO—NH or are absent;

Z is O, S, CO—NH, O—CO—NH or NH—CO—NH or is absent;

m is an integer from 1 to 4;

n is an integer from 1 to 4;

p is an integer from 1 to 6;

q is an integer from 0 to 4, wherein n, p and m are chosen such that the thiol has a total of at least 3, preferably 4 to 6 SH groups.

The above formula is to be understood such that the expressions in brackets can in each case be the same or different when m, p and q respectively are greater than 1. For example, —[Y—$R^2$—Z—$R^3$—(SH)$_n$]$_2$ can represent two identical groups —[Y—$R^2$—Z—$R^3$—(SH)$_n$] or two different groups —[Y—$R^2$—Z—$R^3$—(SH)$_n$] and —[Y'—$R^{2'}$—Z'—$R^{3'}$—(SH)$_{n'}$]. Compounds in which the expressions in brackets have in each case identical meanings are preferred.

The formula extends only to those compounds which are compatible with the theory of chemical valence. For example, when $R^1$ represents a carbon atom, the sum of p and q cannot be greater than three, and m must be one if R is a hydrogen atom. If $R^1$ is absent, the expressions in brackets are linked directly to R. If R is —$SO_2$—, then, if $R^1$ is not absent, m must be 2, and if $R^1$ is absent, the sum of p and q must be 2. If $R^2$ is absent, then preferably Y is also absent, and if $R^3$ is absent, Z is preferably also absent.

The variables of Formula (I) preferably have the following meanings:

R is —$SO_2$—, a linear or branched aliphatic $C_{1-12}$ radical, an aromatic $C_{6-18}$ radical, a cycloaliphatic $C_{5-8}$ radical or a heterocyclic radical with 3 to 5 C atoms, 1 to 3 heteroatoms and a total of 5-8 ring atoms, wherein the heteroatoms are selected from N, O and S;

$R^1$ is absent, a linear or branched aliphatic $C_{1-10}$ radical or an aromatic $C_{6-10}$ radical;

$R^2$ is absent or a linear or branched aliphatic $C_{1-10}$ radical or a phenyl radical;

$R^3$ is a linear or branched aliphatic $C_{1-10}$ radical or a phenyl radical;

$R^4$ is a $C_{1-4}$ alkyl radical;

X is O or is absent;

Y is O or is absent;

Z is O or is absent;

m is 1, 2 or 3;

n is 1 or 2;

p is 1, 2 or 3;

q is 0, 1 or 2.

Quite particularly preferred are thiols of Formula (I) in which the variables have the following meanings:

R is —$SO_2$—, a linear or branched aliphatic $C_{1-6}$ radical, an aromatic $C_6$ radical, a cycloaliphatic $C_{5-8}$ radical or a 1,3,5-triazine-2,4,6-trione radical;

$R^1$ is absent, a linear or branched aliphatic $C_{1-6}$ radical or a phenyl radical;

$R^2$ is absent or a linear or branched aliphatic $C_{1-3}$ radical;

$R^3$ is a linear or branched aliphatic $C_{2-6}$ radical;

$R^4$ is a $C_{1-3}$ alkyl radical;

X is O or is absent;

Y is O or is absent;

Z is O or is absent;

m is 2 or 3;

n is 1;

p is 1 or 2;

q is 0 or 1.

Low-molecular tri- or higher-functionalized mercapto compounds of Formula (I) are partially known and can be easily prepared according to known synthesis methods. For example, tri- or higher-functionalized mercapto compounds are available from corresponding tri- or higher-functionalized allyl compounds by the addition of thioacetic acid and subsequent ester splitting according to methods known in the literature (cf. S. A. Svarovsky, Z. Szekely, J. J. Barchi, Tetrahedron: Asymmetry 16 (2005) 587-598; WO 98/58294 A1; U.S. Pat. No. 4,266,055).

General example (n=1, $R^3$=n-propyl):

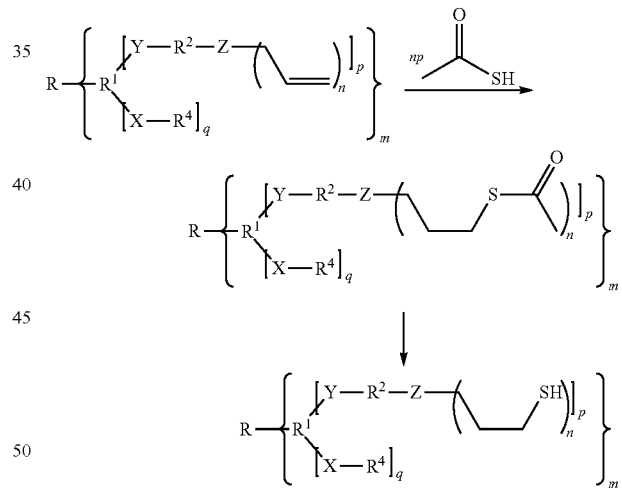

A specific example is:

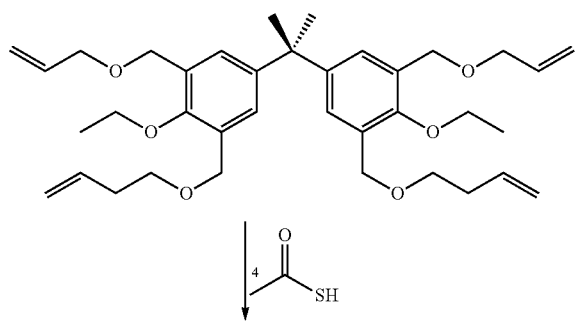

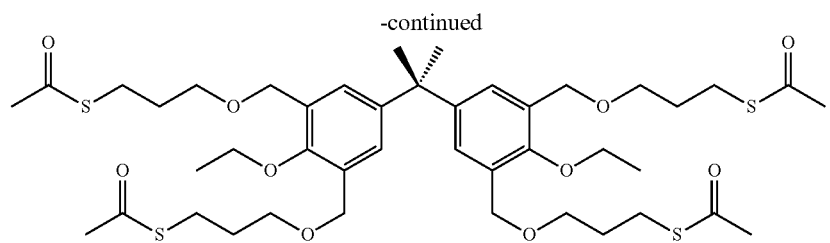

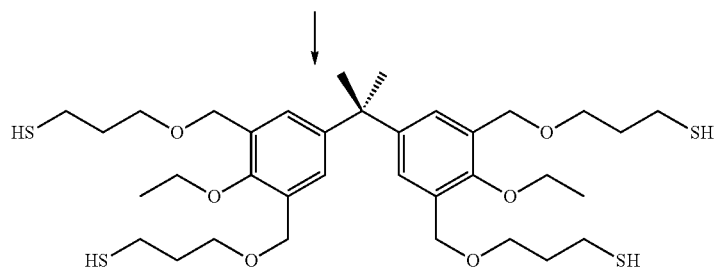

If propargyl derivatives are taken as a starting point, 2 mercapto groups per C—C multiple bond can be introduced simultaneously.

General example (n=2, $R^3$=isopropylene):

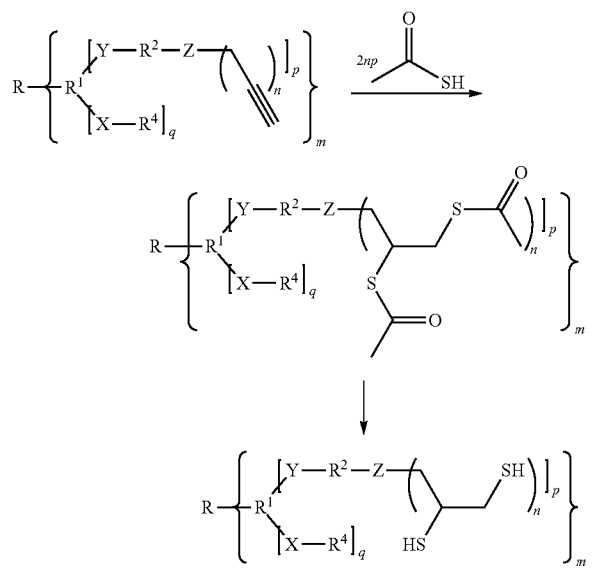

A specific example is:

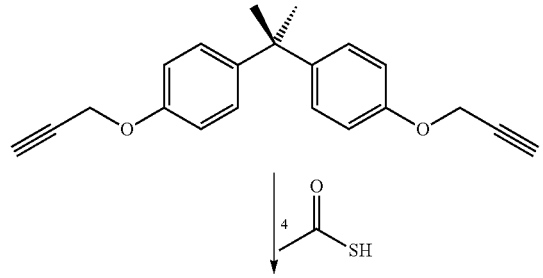

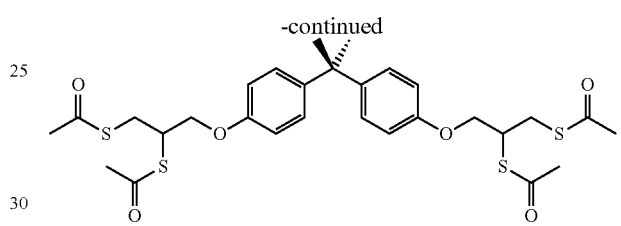

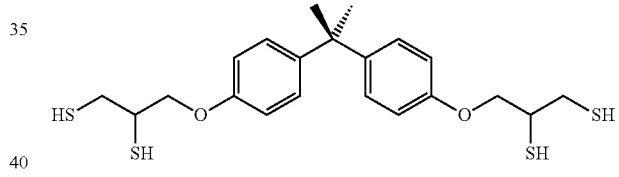

Low-molecular tri- or higher-functionalized mercapto compounds of Formula I can furthermore be prepared by nucleophilic substitution with sulphur nucleophiles such as thiourea etc. from corresponding tri- or higher-functionalized bromine alkanes and subsequent hydrolysis according to methods known in the literature (cf. A. W. Snow, E. E. Foos, Synthesis 4 (2003) 509-512; J. Houk, G. M. Whitesides, J. Am. Chem. Soc. 109 (1987) 6825-6836).

General example (n=2, $R^3$=methylene):

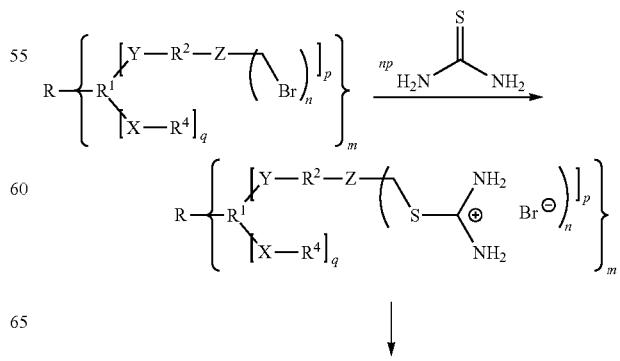

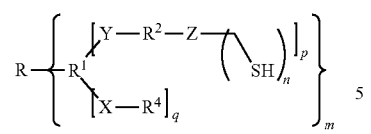
A specific example is:
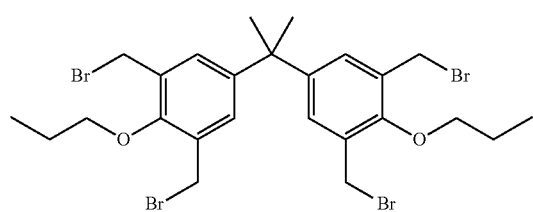
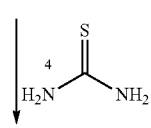
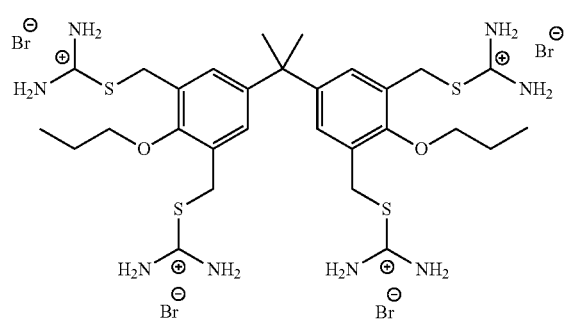
Preferred examples of the tri- or higher-functionalized mercapto compounds, according to the invention, of general Formula I are:
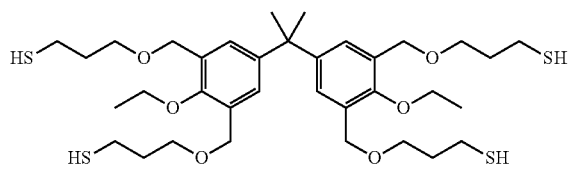
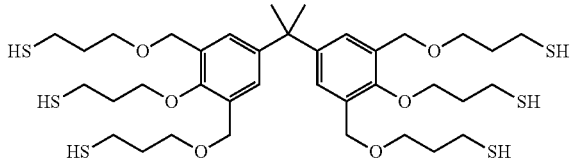
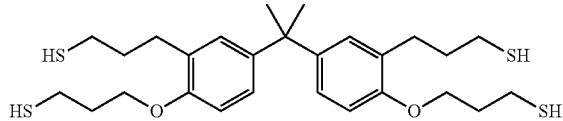
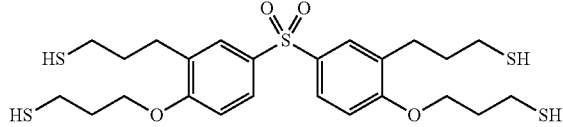
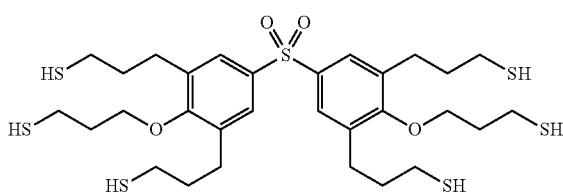
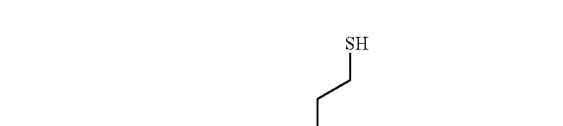
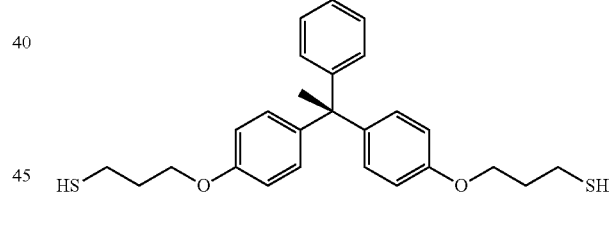
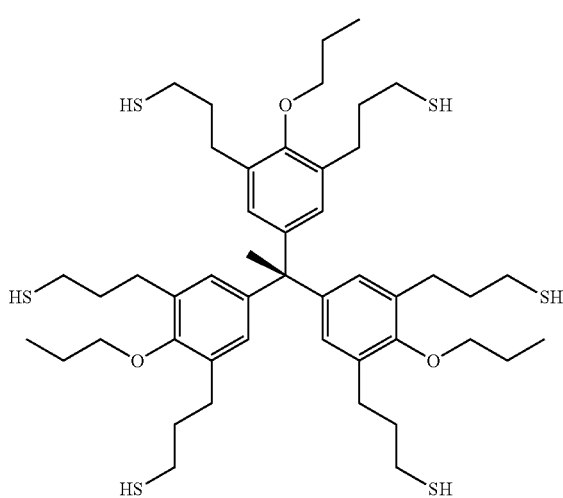

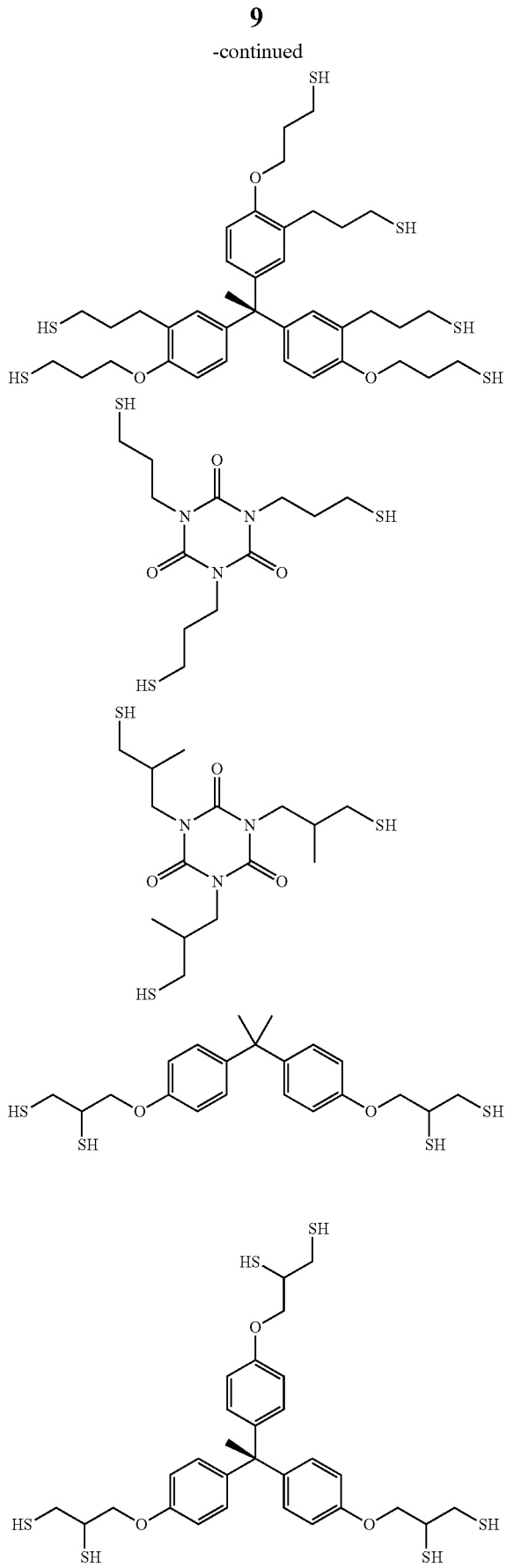
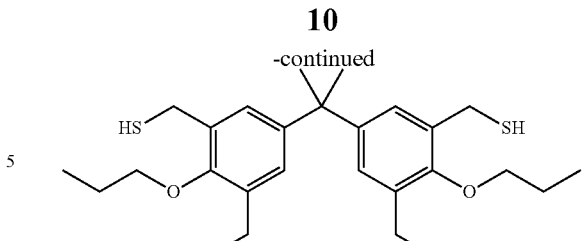

According to a particularly preferred embodiment of the invention, the compounds of Formula (I) are not used directly for preparing dental materials, but are used in the form of a reaction product, e.g. with a di- or multi-functional acrylate or acrylamide or with a di- or multi-functional isocyanate. For this, the thiol of Formula (I) is converted into oligomeric compounds, which are then used as thiol component for preparing dental materials.

The oligomer formation preferably takes place by a nucleophilic thiol-ene reaction or thiol-isocyanate reaction. This involves polyadditions in which the thiol of Formula (I) in a stoichiometric excess in relation to the functional groups is reacted with a di- or multi-functional ene compound or a di- or multi-functional isocyanate. By di- or multi-functional ene compounds and isocyanates are meant compounds with two or more C—C multiple bonds and isocyanate groups respectively. The oligomeric thiols have three or more, preferably 4 to 10 mercapto groups.

The oligomer molar mass can be increased or reduced, with the reaction conversion rate, according to the formula $P_n=(1+1/r)/(1-2p+1/r)$, wherein $P_n$=the average polyaddition rate, r=the molar starting ratio of the thiol and ene groups or isocyanate groups and p=the reaction conversion (100% conversion: p=1). Oligomers with a numerically average molar mass of from 700 to 9,000 g/mol are preferred. In the case of reaction mixtures with a functionality >2, gel formation can occur during the polyaddition, wherein the conversion at which the gel formation begins depends on the stoichiometric ratio of the functional groups and the functionality of the reaction mixture. The gel formation occurs earlier if higher-functionalized mixtures and an approximately stoichiometric ratio of the functional groups are used. Accordingly, it is advantageous for the oligomer formation to use a significant excess of SH groups.

A process for preparing the oligomeric thiol, in which a thiol of Formula (I) in a stoichiometric excess is reacted with a di- or multi-functional ene compound, preferably a di- or multi-functional acrylate or acrylamide, or with a di- or multi-functional isocyanate, is likewise a subject of the invention. The thiol of Formula (I) is preferably reacted with a di- or multi-functional acrylate, di- or multi-functional acrylamide or di- or multi-functional isocyanate in a molar ratio of SH to acryl or NCO groups of from 1.5:1 to 15:1, preferably 1.5:1 to 9:1.

Compounds with electron-poor multiple bonds, such as e.g. di- or multi-functional acrylates and acrylamides, are preferred as ene component for the oligomer formation, because n-electron-poor acrylates and acrylamides, like isocyanates, form oligomers in a rapid nucleophilic polyaddition. Electron-poor multiple bonds are therefore particularly suitable as ene component for the nucleophilic thiol-ene reaction. Electron-poor multiple bonds are those which are linked to electron-withdrawing groups (−M/−I effect).

Preferred ene compounds for the oligomer formation are diacrylates such as bisphenol A diacrylate, bis-GA (an addition product of acrylic acid and bisphenol A diglycidyl ether), ethoxylated or propoxylated bisphenol A diacrylate, UDA (an addition product of 2-hydroxyethyl acrylate and 2,2,4-trimethylhexamethylene diisocyanate), di-, tri- or tetraethylene glycol diacrylate, 1,4-butanediol diacrylate, 1,10-decanediol diacrylate or 1,12-dodecanediol diacrylate. Preferred isocyanates are hexamethylene diisocyanate and 2,2,4-trimethylhexamethylene diisocyanate.

Oligomeric mercapto compounds can be synthesized for example by nucleophilic thiol-ene reactions, known in the literature, of di- or multi-functional acrylates or acrylamides with tri- or higher-functionalized mercapto compounds (cf. J. W. Chan, C. E. Hoyle, A. B. Lowe, M. Bowman, Macromolecules 43 (2010) 6381-6388; G.-Z. Li, R. K. Randex, A. H. Soeriyadi, G. Rees, C. Boyer, Z. Tong, Polym. Chem. 1 (2010) 1196-1204; B. D. Mather, K. Viswanathan, K. M. Miller, T. E. Long, Prog. Polym. Sci. 31 (2006) 487-531).

GENERAL EXAMPLE

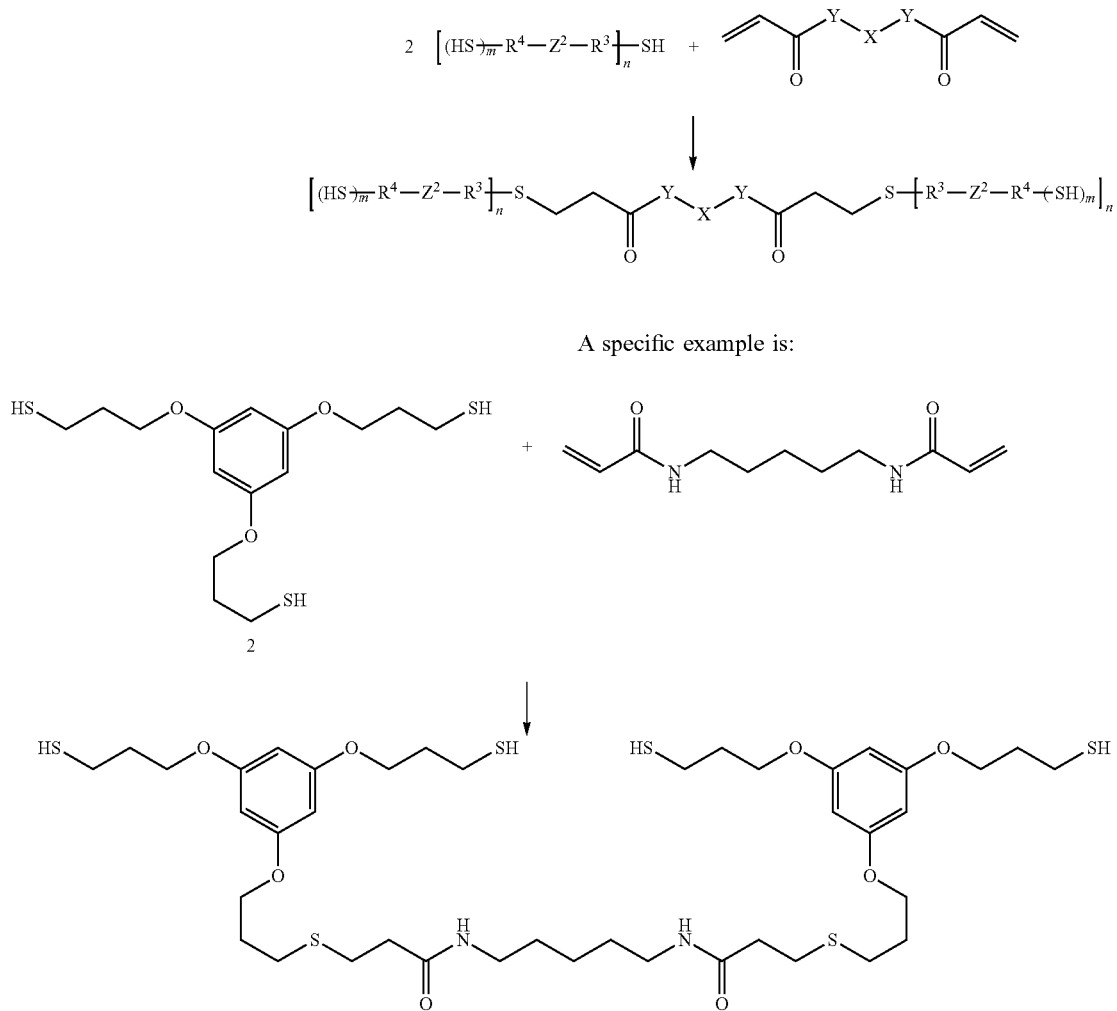

A specific example is:

Oligomeric mercapto compounds can likewise be synthesized by nucleophilic thiol-isocyanate reaction, known in the literature, of di- or multi-functional isocyanates with tri- or higher-functionalized mercapto compounds (cf. H. Li., B. Yu, H. Matsushima, C. E. Hoyle, A. B. Lowe, Macromolecules 42 (2009) 6537-6542).

GENERAL EXAMPLE

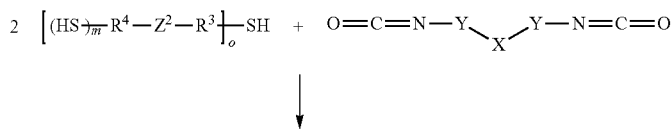

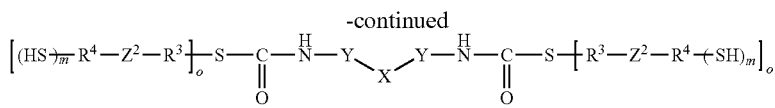

A specific example is:

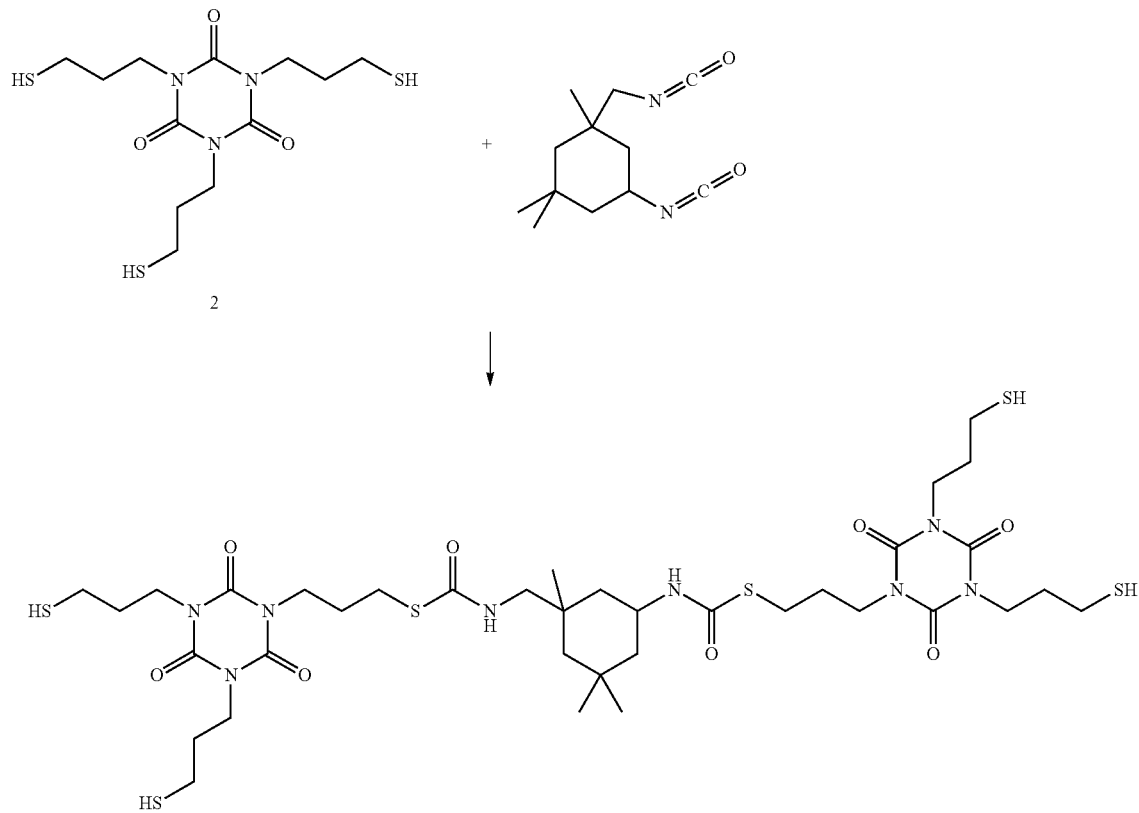

For preparing dental materials, one or more thiols of Formula (I) or oligomeric thiols based thereon are combined with at least one compound which contains three or more C—C multiple bonds (ene component). Here, compounds with electron-rich multiple bonds, such as e.g. n-electron-rich vinyl, allyl or norbornene compounds as well as alkynes, are preferred as ene component. Electron-rich ene compounds yield storage-stable mixtures with SH compounds and can be rapidly cured by radical polyaddition. Electron-rich multiple bonds are those which are linked to electron-donating groups (+M/+I effect).

Above all, vinyl ethers, vinyl esters and N-vinyl amides, for example trimethylolpropane trivinyl ether or pentaerythritol tetravinyl ether, are suitable as electron-rich vinyl compounds.

Among others, allyl ethers of tri- or higher-functionalized alcohols, such as for example trimethylolpropane triallyl ether or pentaerythritol tetraallyl ether, can be used as electron-rich allyl compounds. For example reaction products of tri- or higher-functionalized carboxylic acids with allyl alcohol or allylamine or also other tri- or higher-functionalized allyl compounds such as e.g. triallylamine or triallyl-1,3,5-triazine-2,4,6-trione (TATATO) are also suitable.

Among others, the esters of 5-norbornene-2-carboxylic acid with tri- or higher-functionalized alcohols or esters of 5-norbornene-2-methanol with tri- or higher-functionalized carboxylic acids can be used as norbornene compounds. Examples are trimethylolpropanetriol tri-(5-norbornene-2-carboxylic acid) ester or benzene-1,3,5-tricarboxylic acid tri-(5-norbornene-2-methanol) ester.

Among others, esters of propargyl alcohol with tri- or higher-functionalized carboxylic acids or ethers of propargyl alcohol with tri- or higher-functionalized alcohols can be used as tri- or higher-functionalized alkynes. Examples are benzene-1,3,5-tricarboxylic acid tripropargyl ester or pentaerythritol tetrapropargyl ether.

Particularly preferred electron-rich ene compounds are tri- or higher-functionalized allyl compounds, preferably triallyl-1,3,5-triazine-2,4,6-trione (TATATO).

In addition, the dental materials according to the invention can preferably also contain mono- or multi-functional methacrylates or mixtures thereof as comonomers. By monofunctional methacrylates are meant compounds with one, by polyfunctional methacrylates compounds with two or more, preferably 2 to 4, radically polymerizable groups. The dental materials preferably contain no free acrylates or acrylamides, because these can adversely affect the storage stability because of their high SH reactivity.

Examples of mono- or multi-functional methacrylates are methyl, ethyl, 2-hydroxyethyl, butyl, benzyl, tetrahydrofurfuryl or isobornyl methacrylate, p-cumylphenoxyethyleneglycol methacrylate (CMP-1E), bisphenol A dimethacrylate, bis-GMA (an addition product of methacrylic acid and bisphenol A diglycidyl ether), ethoxylated or propoxylated bisphenol A dimethacrylate, such as e.g. the bisphenol A dimethacrylate SR-348c (Sartomer) with 3 ethoxy groups or 2,2-bis[4-(2-methacryloxypropoxy)phenyl]propane, UDMA (an addition product of 2-hydroxyethyl methacrylate and 2,2,4-trimethylhexamethylene diisocyanate), di-, tri- or tetraethylene glycol dimethacrylate, trimethylolpropane trimethacrylate, pentaerythritol tetramethacrylate, as well as glycerol di- and trimethacrylate, 1,4-butanediol dimethacrylate, 1,10-decanediol dimethacrylate ($D_3MA$) or 1,12-dodecanediol dimethacrylate.

Furthermore, the dental materials preferably contain an initiator for the radical polymerization. The dental materials according to the invention can be cured by thermal, redox-initiated or light-induced radical polymerization. In the case of indirect filling materials, thermal initiators such as e.g. dibenzoyl peroxide (DBPO) or derivatives of barbituric acid, such as e.g. trimethyl barbituric acid, are preferably used. Redox-initiator systems, such as e.g. combinations of DBPO with N,N-dimethyl-sym.-xylidine or N,N-dimethyl-p-toluidine, are preferably used as initiators for a polymerization carried out at room temperature.

The dental materials according to the invention preferably contain a photoinitiator, preferably benzophenone, benzoin as well as derivatives thereof or α-diketones or derivatives thereof, such as 9,10-phenanthrenequinone, 1-phenylpropane-1,2-dione, diacetyl or 4,4'-dichlorobenzil, are used. Preferably camphorquinone or 2,2-dimethoxy-2-phenyl-acetophenone and particularly preferably α-diketones combined with amines as reducing agents, such as e.g. 4-(dimethylamino)-benzoate, N,N-dimethylaminoethyl methacrylate, N,N-dimethyl-sym.-xylidine or triethanolamine, are used. Norrish type I photoinitiators, above all acyl or bisacyl phosphine oxides, are also very suitable, and monoacyltrialkyl or diacyldialkyl germanium compounds, such as e.g. benzoyltrimethyl germanium, dibenzoyl diethyl germanium or bis(4-methoxybenzoyl)diethyl germanium, are particularly suitable. Mixtures of the different photoinitiators can also be used, such as e.g. bis(4-methoxybenzoyl) diethyl germanium combined with camphorquinone and 4-dimethylaminobenzoic acid ethyl ester.

According to a preferred embodiment the dental materials according to the invention additionally contain organic or preferably inorganic particulate filler.

Fillers based on oxides with a particle size of from 0.1 to 1.5 μm, such as $SiO_2$, $ZrO_2$ and $TiO_2$ or mixed oxides of $SiO_2$, $ZrO_2$, ZnO and/or $TiO_2$, nanoparticulate or microfine fillers with a particle size of from 0.01 to 500 nm, such as pyrogenic silicic acid or precipitated silicic acid as well as glass powder with a particle size of from 0.01 to 15 μm, preferably from 0.2 to 1.5 μm, such as quartz, glass-ceramic or X-ray opaque glass powder of e.g. barium or strontium aluminium silicate glasses, and X-ray opaque fillers with a particle size of from 0.2 to 1.5 μm, such as ytterbium trifluoride, tantalum(V) oxide, barium sulphate or mixed oxides of $SiO_2$ with ytterbium(III) oxide or tantalum(V) oxide, are particularly suitable. Fibrous fillers, nanofibres or whiskers are also not excluded. Unless otherwise indicated, all particle sizes are weight-average particle sizes.

The fillers are divided, according to particle size, into macrofillers and microfillers. Macrofillers are obtained by grinding quartz, X-ray opaque glasses, borosilicates or ceramic, are of a purely inorganic nature and mostly consist of splinter-like parts. Macrofillers with an average particle size of from 0.2 to 10 μm are preferred. Pyrogenic $SiO_2$ or precipitated silicic acid are preferably used as microfillers, or also mixed oxides, e.g. $SiO_2$—$ZrO_2$, which are available by hydrolytic co-condensation of metal alkoxides. The microfillers preferably have an average particle size of from approx. 5 to 100 nm.

The dental materials according to the invention can also contain so-called microfiller complexes. Examples of these are splinter-like microfilled polymers, which are available e.g. by incorporating inorganic fillers such as e.g. pyrogenic $SiO_2$ in a resin matrix, subsequent thermal polymerization of the mixture and grinding of the thus-obtained polymer.

Fibrous fillers are used in particular to prepare framework materials.

To improve the bond between the filler particles and the cross-linked polyaddition matrix, $SiO_2$-based fillers can be surface-modified with thiol-, vinyl-, allyl-, norborn-2-enyl-, methacryl- or alkyne-functionalized silanes. Examples of such silanes are 3-thiopropyltrimethoxysilane, 3-allyltriethoxysilane, 3-methacryloxypropyltrimethoxysilane or N-[3-(triethoxysilyl)-propyl]carbamic acid propargyl ester. For the surface modification of non-siliceous fillers such as e.g. $ZrO_2$ or $TiO_2$, functionalized acidic phosphates, such as e.g. allyl or propargyl dihydrogen phosphate, can also be used.

The fill level is geared to the desired intended use. Filling composites preferably have a filler content of 75-90 wt.-% and composite cements a filler content of 50-75 wt.-%.

Optionally, the compositions used according to the invention can contain further additives, above all stabilizers, dyes, microbiocidal active ingredients, fluoride-ion-releasing additives, optical brighteners, plasticizers and/or UV absorbers, in particular inhibitors, UV stabilizers and pigments.

According to the invention, dental materials which contain the following components are preferred:
a) 5 to 40 wt.-%, preferably 5 to 30 wt.-% and particularly preferably 5 to 20 wt.-% thiol of general Formula I or an oligomer thereof,
b) 5 to 40 wt.-%, preferably 5 to 30 wt.-% and particularly preferably 5 to 20 wt.-% ene component,
c) 0 to 40 wt.-%, preferably 2 to 30 wt.-% and particularly preferably 4 to 20 wt.-% methacrylate(s),
d) 0.01 to 10 wt.-%, particularly preferably 0.1 to 3.0 wt.-% initiator,
e) 10 to 85 wt.-% filler, and
f) 0 to 10 wt.-%, preferably 0 to 5 wt.-% additives.

Those dental materials that consist of the named components are particularly preferred. Furthermore, those materials in which the individual components are in each case selected from the above-named preferred and particularly preferred substances are preferred. Materials which, in addition to the thiol of Formula (I) or an oligomer thereof, do not contain volatile mercaptans, i.e. mercaptans which have a typical mercaptan odour, are particularly preferred. Compositions which do not contain further mercaptans and preferably also do not contain other sulphur compounds are quite particularly preferred.

The dental materials according to the invention are particularly suitable as dental cements, filling composites and veneering materials, and as materials for preparing inlays, onlays, crowns and bridges. They are characterized by a high conversion of the polyreactive groups, similar mechanical properties to materials based on dimethacrylates, a reduced polymerization stress, low inherent odour and odour-stable properties even after a long storage. Moreover, they have a low polymerization shrinkage.

The dental materials are primarily suitable for intraoral use by the dentist to restore damaged teeth (clinical materials). However, they can also be used extraorally, for example in the preparation or repair of dental restorations (technical materials).

The invention is explained in more detail below by means of embodiment examples.

EMBODIMENT EXAMPLES

Example 1

Synthesis of a Tetrathiol-Functionalized Bisphenol a Derivative by Radical Addition of Thioacetic Acid on an Allyl Precursor a) Synthesis of 2,2-bis[3-(3-acetylmercaptopropyl)-4-(3-acetylmercaptopropoxy)-phenyl]propane

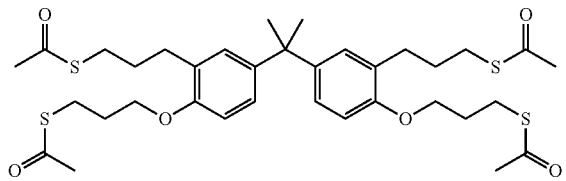 [SMILES: CC(=O)SCCCOc1ccc(C(C)(C)c2ccc(OCCCSC(C)=O)c(CCCSC(C)=O)c2)cc1CCCSC(C)=O]

29.14 g (75 mmol) 2,2-bis[3-allyl-4-allyloxyphenyl]propane, which is available according to instructions known in the literature (cf. patent WO 98/58294 A1; M. Abraham, I. Hamerton, J. Rose, J. Grate, J. Chem. Soc. Perkin Trans. 2 (1991) 1417-1423) from bisphenol A and allyl bromide by means of Williamson ether synthesis and Claisen rearrangement, 34.25 g (450 mmol) thioacetic acid and 2.46 g (15 mmol) 2,2'-azobis(2-methylpropionitrile) in 200 mL tetrahydrofuran were introduced into a 500-mL three-necked flask. The reaction solution was rinsed with nitrogen for 30 min and then stirred under nitrogen atmosphere for 16 hours at 65° C. After cooling of the reaction solution in an ice bath, 100 mL of a one molar sodium carbonate solution was added dropwise. After extraction with dichloromethane three times, the combined organic phases were washed twice with a one molar sodium hydroxide solution as well as saturated sodium chloride solution, dried over magnesium sulphate and freed from the solvent on a rotary evaporator under reduced pressure. The crude product was purified by column chromatography over silica gel in order to obtain 35.8 g (51.7 mmol, 69% theoretical) 2,2-bis[3-(3-acetylmercaptopropyl)-4-(3-acetylmercaptopropoxy)-phenyl]propane as a yellow, highly viscous oil.

$^1$H NMR (300 MHz, CDCl$_3$, δ [ppm]): 7.02-6.92 (m, 4H, ArH), 6.69 (d, $^3J_{HH}$=8.5 Hz, 2H, ArH), 3.98 (t, $^3J_{HH}$=5.9 Hz, 4H, OCH$_2$), 3.07 (t, $^3J_{HH}$=7.1 Hz, 4H, CH$_2$S), 2.85 (t, $^3J_{HH}$=7.2 Hz, 4H, CH$_2$S), 2.63 (m, 4H, ArCH$_2$), 2.34 and 2.32 (s, 12H, CH$_3$), 2.14-2.01 (m, 4H, CH$_2$), 1.90-1.75 (m, 4H, CH$_2$), 1.61 (s, 6H, C(CH$_3$)$_2$);

$^{13}$C NMR (75 MHz, CDCl$_3$, δ [ppm]): 196.01 and 195.81 (S(C=O)CH$_3$), 154.50 (ArC), 143.08 (ArC), 128.98 (ArC), 128.90 (ArC), 125.39 (ArC), 110.48 (ArC), 66.12 (ArOCH$_2$), 41.75 (C(CH$_3$)$_2$), 31.26 (C(CH$_3$)$_2$), 30.80 (S(C=O)CH$_3$), 29.98 (CH$_2$), 29.83 (CH$_2$), 29.64 (CH$_2$), 29.05 (CH$_2$), 26.24 (CH$_2$);

FTIR: ν=2962 (w), 2926 (w), 2867 (w), 1685 (s, ν$_{C=O}$), 1607 (w), 1500 (s), 1470 (m), 1415 (m), 1410 (m), 1383 (w), 1353 (m), 1294 (w), 1243 (s), 1131 (s), 1105 (s), 1038 (m), 953 (s) cm$^{-1}$;

MALDI-TOF MS: m/z$_{found}$: 692.2 (M$^+$), 715.2 (M+Na$^+$), 731.2 (M+K$^+$), m/z$_{calculated}$: 715.22 (M+Na$^+$).

b) Synthesis of 2,2-bis[3-(3-mercaptopropyl)-4-(3-mercaptopropoxy)phenyl]-propane

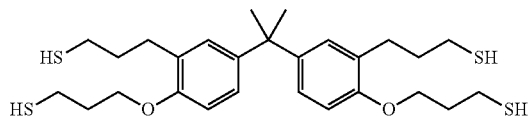 [SMILES: CC(C)(c1ccc(OCCCS)c(CCCS)c1)c1ccc(OCCCS)c(CCCS)c1]

35.69 g (51.50 mmol) 2,2-bis[3-(3-acetylmercaptopropyl)-4-(3-acetylmercaptopropoxy)-phenyl]propane, 22.17 g conc. hydrochloric acid (37 wt.-%) in a mixture of 200 mL methanol and 50 mL tetrahydrofuran were introduced into a 500-mL three-necked flask. The reaction solution was rinsed thoroughly with nitrogen for 30 min and then stirred under a nitrogen atmosphere for 20 hours at 60° C. After cooling to room temperature, 150 mL distilled water was added. After extraction with dichloromethane three times, the combined organic phases were washed twice with a one molar sodium hydroxide solution as well as saturated sodium chloride solution, dried over magnesium sulphate and freed from the solvent on a rotary evaporator under reduced pressure. The crude product was purified by column chromatography over silica gel in order to obtain 20.8 g (39.6 mmol, 76% theoretical) 2,2-bis[3-(3-mercaptopropyl)-4-(3-mercaptopropoxy)phenyl]-propane as a highly viscous oil after drying in a fine vacuum.

$^1$H NMR (300 MHz, CDCl$_3$, δ [ppm]): 7.02 (dd, $^3J_{HH}$=8.6 Hz/$^4J_{HH}$=2.5 Hz, 2H, ArH), 6.94 (d, $^4J_{HH}$=2.5 Hz, 2H, ArH), 6.73 (d, $^3J_{HH}$=8.5 Hz, 2H, ArH), 4.04 (t, $^3J_{HH}$=5.8 Hz, 4H, OCH$_2$), 2.79-2.70 (m, 4H, CH$_2$SH), 2.69-2.61 (m, 4H, ArCH$_2$), 2.53-2.42 (m, 4H, CH$_2$SH), 2.14-2.03 (m, 4H, CH$_2$), 1.90-1.77 (m, 4H, CH$_2$), 1.61 (s, 6H, C(CH$_3$)$_2$), 1.40 (t, $^3J_{HH}$=8 0.1 Hz, 2H, SH), 1.34 (t, $^3J_{HH}$=7.8 Hz, 2H, SH);

$^{13}$C NMR (75 MHz, CDCl$_3$, δ [ppm]): 154.54 (ArC), 143.05 (ArC), 129.08 (ArC), 129.04 (ArC), 125.22 (ArC), 110.52 (ArC), 65.55 (OCH$_2$), 41.74 (C(CH$_3$)$_2$), 34.30 (CH$_2$), 33.65 (CH$_2$), 31.26 (C(CH$_3$)$_2$) 29.42 (CH$_2$), 24.45 (CH$_2$), 21.62 (CH$_2$);

FTIR: ν=3050 (w), 3025 (w), 2961 (m), 2925 (m), 2867 (w), 2560 (w, ν$_{SH}$), 1606 (w), 1499 (s), 1468 (m), 1439 (m), 1383 (w), 1360 (w), 1294 (m), 1242 (s), 1181 (m), 1154 (m), 1117 (m), 1034 (m), 810 (s) cm$^{-1}$; MS (EI) m/z (%): 525 (12) [M$^+$], 524 (36) [M$^+$], 511 (21), 510 (30), 509 (100), 450 (18), 437 (13), 436 (20), 435 (78), 362 (17), 361 (76), 327 (12), 287 (25), 213 (19), 209 (28), 207 (10), 193 (18), 179 (12), 175 (34), 159 (26), 147 (35), 135 (21), 133 (11), 119 (16), 107 (12), 75 (12), 47 (14), 41 (19);

Elemental Analysis calculated for C$_{27}$H$_{40}$O$_2$S$_4$: C, 61.79; H, 7.68; S, 24.44. found: C, 61.99; H, 7.62; S, 24.65.

Example 2

Synthesis of a Tetrathiol-Functionalized Bisphenol A Derivative by Using the Radical Addition of Thioacetic Acid on Propargyl Groups a) Synthesis of 2,2-bis[4-(2,3-diacetylmercaptopropoxy)-phenyl]propane

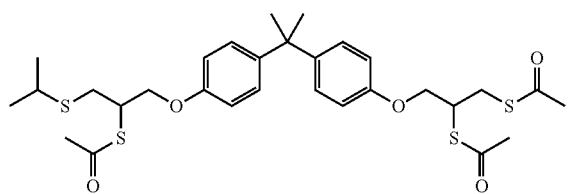 [SMILES: CC(=O)SCC(COc1ccc(C(C)(C)c2ccc(OCC(CSC(C)C)SC(C)=O)cc2)cc1)SC(C)=O]

10.65 g (35 mmol) 2,2-bis[4-(prop-2-yn-1-yloxy)phenyl]propane, which is available by a Williamson ether synthesis from bisphenol A and propargyl bromide, 26.64 g (350 mmol) thioacetic acid, 1.38 g (8.4 mmol) 2,2'-azobis(2-methylpropionitrile) and 150 mL toluene were introduced into a 250-mL three-necked flask. The reaction solution was rinsed thoroughly with nitrogen for 30 min and then stirred under a permanent nitrogen atmosphere for 24 hours at 65° C. After removal of the volatile components under reduced pressure, the crude product was purified by column chromatography over silica gel. In this way, 16.0 g (26.3 mmol, 75% theoretical) 2,2-bis[4-(2,3-diacetylmercaptopropoxy)phenyl]propane was obtained as a highly viscous yellow oil.

$^1$H NMR (300 MHz, CDCl$_3$, δ [ppm]): 7.10 (d, $^3J_{HH}$=8.9 Hz, 4H, Ar—H), 6.78 (d, $^3J_{HH}$=8.9 Hz, 4H, Ar—H), 4.20-4.10 (m, 2H, —CH—), 4.05-3.94 (m, 4H, —OCH$_2$—), 3.45-3.19 (m, 4H, —CH$_2$S—), 2.33 (s, 3H, —CH$_3$), 2.32 (s, 3H, —CH$_3$), 1.60 (s, 6H, —C(CH$_3$)$_2$);

$^{13}$C NMR (75 MHz, CDCl$_3$, δ [ppm]): 194.70 (—S(C═O)CH$_3$), 194.61 (—S(C═O)CH$_3$), 156.25 (Ar—C4), 143.85 (Ar—C1), 127.92 (Ar—C2,C6) 114.16 (Ar—C3, C5), 68.73 (Ar—OCH$_2$—), 43.52 (—CH—), 41.88 (—C(CH$_3$)$_2$) 31.16 (—CH$_2$S—), 30.79 (—C(CH$_3$)$_2$) 30.68 (—CH$_3$), 30.58 (—CH$_3$);

FTIR: ν=3035 (m), 2966 (m), 2930 (m), 2861 (m), 1688 (s, ν$_{C═O}$), 1607 (m, ν$_{C═C}$), 1582 (w, ν$_{C═C}$), 1508 (s, ν$_{C═C}$), 1463 (m), 1410 (m), 1383 (m), 1353 (m), 1297 (m), 1237 (s), 1181 (s), 1127 (s), 1105 (s) cm$^{-1}$;

MALDI-TOF MS: m/z$_{found}$: 631.1 [M+Na$^+$]; m/z$_{calculated}$: 631.13 [M+Na$^+$].

b) Synthesis of 2,2-bis[4-(2,3-dimercaptopropoxy)phenyl]propane

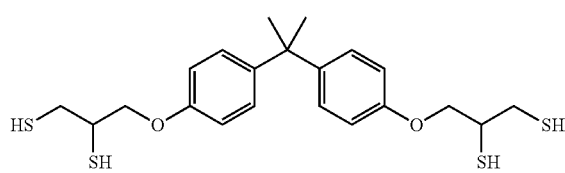 [SMILES: CC(C)(c1ccc(OCC(S)CS)cc1)c1ccc(OCC(S)CS)cc1]

14.92 g (24.50 mmol) 2,2-bis[4-(2,3-diacetylmercaptopropoxy)-phenyl]propane was dissolved in 40 mL THF in a 250-mL two-necked flask and continuously rinsed thoroughly with nitrogen. The dropwise addition of 60 mL of a potassium methoxide solution (25 wt.-%) took place in an ice bath at 0° C. After addition was complete, the solution was stirred for a further 30 min in an ice bath and then added to 100 mL of a 1N ice-cold HCl solution. The suspension was transferred to a separating funnel and shaken out three times with dichloromethane. The combined organic phases were washed with 100 mL saturated sodium chloride solution, dried over MgSO$_4$ and freed from the solvent. The crude product was purified by column chromatography over silica gel in order to obtain 6.5 g (14.7 mmol, 60% theoretical) 2,2-bis[4-(2,3-dimercaptopropoxy)-phenyl]propane as a colourless solid. Melting point: 85° C.;

$^1$H NMR (300 MHz, CDCl$_3$, δ [ppm]): 7.13 (d, $^3J_{HH}$=8.9 Hz, 4H, Ar—H), 6.80 (d, $^3J_{HH}$=8.9 Hz, 4H, Ar—H), 4.17 (dd, $^3J_{HH}$=4.7 Hz/$^2J_{HH}$=9.6 Hz, 2H, Ar—OCHH—), 4.02 (dd, $^3J_{HH}$=7.3 Hz/$^2J_{HH}$=9.6 Hz, 2H, Ar—OCHH—), 3.32-3.20 (m, 2H, —CH—), 3.00-2.92 (m, 4H, —CH$_2$SH), 1.95 (d, $^3J_{HH}$=9.2 Hz, 2H, 1.65-1.56 (m, 8H, —C(CH$_3$)$_2$ and —CH$_2$SH);

$^{13}$C NMR (75 MHz, CDCl$_3$, δ [ppm]): 156.23 (Ar—C4), 143.91 (Ar—C1), 128.01 (Ar—C2,C6), 114.21 (Ar—C3, C5), 70.19 (Ar—OCH$_2$—), 41.93 (—C(CH$_3$)$_2$), 41.70 (—CH—), 31.21 (—C(CH$_3$)$_2$) 29.98 (—CH$_2$SH);

FTIR: ν=3060 (w), 3036 (w), 2962 (m), 2932 (m), 2866 (m), 2557 (m, ν$_{SH}$), 1607 (m), 1581 (w), 1508 (s), 1455 (s), 1414 (m), 1378 (m), 1362 (m), 1300 (s), 1232 (s), 1180 (s) cm$^{-1}$;

MS (EI) m/z (%): 440 (3) [M$^+$], 228 (32), 214 (15), 213 (100), 135 (12), 73 (13).

Example 3

Synthesis of a Thiol Resin by Addition of a Trithiol-Functional Precursor on 1,4-butanediol diacrylate or tricyclo-[5.2.1.0(2.6)]decanedimethylol-diacrylate (TCD-DA)

a) Synthesis of 1,3,5-tris(3-acetylmercaptopropyl)-1,3,5-triazine-2,4,6-trione

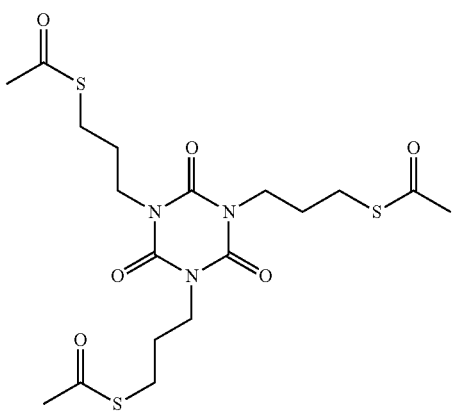 [SMILES: CC(=O)SCCCn1c(=O)n(CCCSC(C)=O)c(=O)n(CCCSC(C)=O)c1=O]

In a 500-mL three-necked flask, 37.39 g (150 mmol) 1,3,5-triallyl-1,3,5-triazine-2,4,6-trione, 41.10 g (540 mmol) thioacetic acid and 3.69 g (22.5 mmol) 2,2'-azobis(2-methylpropionitrile) were dissolved in 250 mL tetrahydrofuran analogously to U.S. Pat. No. 4,266,055. The reaction solution was rinsed thoroughly with nitrogen for 30 min and then heated under nitrogen atmosphere for 16 hours at 65° C.

After cooling of the reaction solution in an ice bath to 0° C., 100 mL of a one molar sodium carbonate solution was added dropwise. After extraction with dichloromethane three times, the combined organic phases were washed with 80 mL of a one molar sodium hydroxide solution as well as saturated sodium chloride solution, dried over magnesium sulphate and freed from the solvent on a rotary evaporator under reduced pressure. The crude product was recrystallized three times from 200 mL methanol in order to obtain 1,3,5-tris(3-acetylmercaptopropyl)-1,3,5-triazine-2,4,6-trione (48.0 g, 100.5 mmol, 67% theoretical) as a colourless and odourless solid. Melting point: 66-67° C.;

$^1$H NMR (300 MHz, CDCl$_3$, δ [ppm]): 3.89 (t, $^3J_{HH}$=7.1 Hz, 6H, —NCH$_2$—), 2.83 (t, $^3J_{HH}$=7.1 Hz, 6H, —CH$_2$S—), 2.26 (s, 9H, —CH$_3$), 1.87 (quint., $^3J_{HH}$=7.1 Hz, 6H, —CH$_2$—);

$^{13}$C NMR (75 MHz, CDCl$_3$, δ [ppm]): 195.45 (—S(C=O)CH$_3$), 149.03 (—C=O), 42.07 (—NCH$_2$—), 30.68 (—CH$_3$), 28.03 (—CH$_2$—), 26.27 (—CH$_2$S—);

FTIR: ν=3024 (w), 2977 (m), 2945 (w), 2923 (w), 1692 (s, ν$_{C=O}$), 1676 (s, ν$_{C=O}$), 1508 (w), 1457 (s), 1425 (s), 1373 (m), 1352 (m), 1338 (m), 1327 (m), 1307 (m), 1296 (w), 1283 (w), 1242 (w), 1135 (s), 1107 (s), 1045 (w), 955 (m), 763 (s, ν$_{C-S}$) cm$^{-1}$;

MS (EI) m/z (%): 519 (4) [M+], 477 (16), 476 (32), 444 (12), 434 (14), 402 (26), 400 (12), 390 (11), 360 (24), 358 (22), 348 (42), 326 (12), 314 (12), 306 (50), 272 (40), 184 (16), 130 (23), 96 (10), 87 (19), 56 (15), 55 (17), 43 (100), 41 (10).

b) Synthesis of 1,3,5-tris(3-mercaptopropyl)-1,3,5-triazine-2,4,6-trione

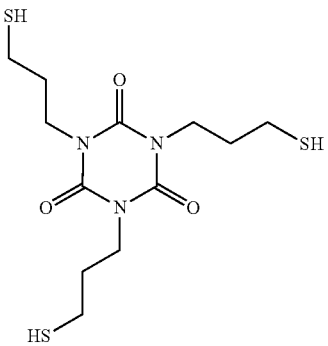 [SMILES: O=c1n(CCCS)c(=O)n(CCCS)c(=O)n1CCCS]

In a 500-mL three-necked flask, 44.89 g (94 mmol) 1,3,5-tris(3-acetylmercaptopropyl)-1,3,5-triazine-2,4,6-trione was dissolved in a mixture of 190 mL methanol and 60 mL 1,4-dioxane. This solution was rinsed thoroughly with nitrogen for 30 min and then 29.43 g concentrated hydrochloric acid solution (37 wt.-%) was added. The reaction solution was stirred under a nitrogen atmosphere for 20 hours at 60° C. After cooling to room temperature, 200 mL distilled water was added and the aqueous phase was extracted three times with dichloromethane. The combined organic phases were washed with two times 100 mL saturated sodium hydrogen carbonate solution as well as sodium chloride solution, dried over magnesium sulphate and freed from the solvent after filtration on a rotary evaporator under reduced pressure. 32.2 g (91.6 mmol, 97% theoretical) 1,3,5-tris(3-mercaptopropyl)-1,3,5-triazine-2,4,6-trione was obtained as a low-odour, colourless oil (zero shear viscosity at 25° C.: approx. 5 Pa*s). A further reduction in odour was possible by filtration over silica gel.

$^1$H NMR (300 MHz, CDCl$_3$, δ [ppm]): 4.01 (t, $^3J_{HH}$=7.0 Hz, 6H, —NCH$_2$—), 2.56 (dt, $^3J_{HH}$=6.9 Hz/$^3J_{HH}$=8.0 Hz, 6H, —CH$_2$S—), 1.97 (quint., $^3J_{HH}$=7.0 Hz, 6H, —CH$_2$—), 1.54 (t, $^3J_{HH}$=8.0 Hz, 6H, —CH$_2$SH);

$^{13}$C NMR (75 MHz, CDCl$_3$, δ [ppm]): 149.10 (—C=O), 41.91 (—NCH$_2$—), 31.94 (—CH$_2$—), 22.03 (—CH$_2$SH);

FTIR: ν=2963 (w), 2933 (w), 2857 (w), 2568 (w, ν$_{SH}$), 1671 (s, ν$_{C=O}$), 1502 (w), 1454 (s), 1422 (s), 1374 (m), 1334 (m), 1318 (m), 1288 (m), 1258 (m), 762 (s, ν$_{C-S}$) cm$^{-1}$;

MS (EI) m/z (%): 351 (22) [M$^+$], 319 (19), 318 (85), 317 (34), 286 (17), 284 (100), 244 (20), 224 (25), 210 (49), 170 (27), 127 (21), 84 (29), 70 (41), 56 (77), 47 (22), 41 (35);

Elemental Analysis
calculated for C$_{12}$H$_{21}$N$_3$O$_3$S$_3$: C, 41.00; H, 6.02; N, 11.95; S, 27.37.
found: C, 41.02; H, 5.92; N, 11.84; S, 27.48.

c) Thiol-Michael Addition of 1,4-butanediol diacrylate and 1,3,5-tris(3-mercaptopropyl)-1,3,5-triazine-2,4,6-trione

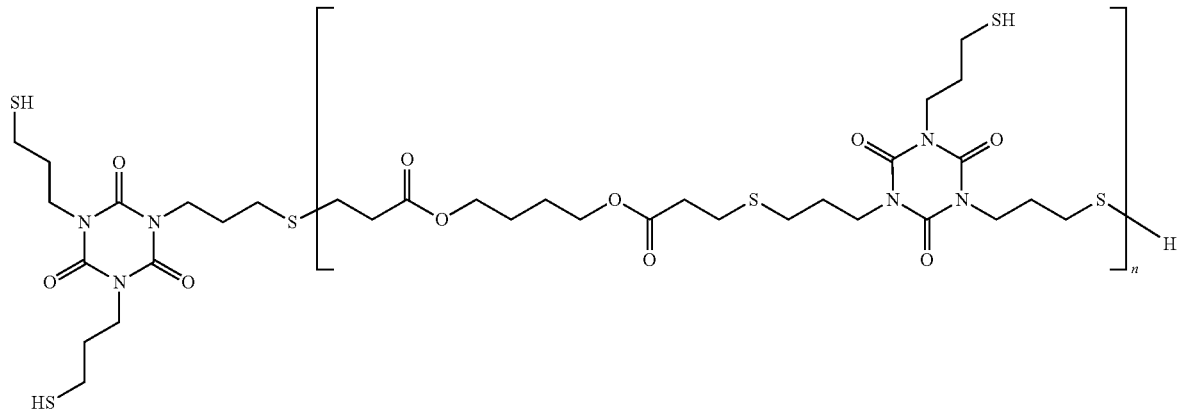

In a 10-mL microwave pressure vial with a septum, 1.05 g (3 mmol) 1,3,5-tris(3-mercaptopropyl)-1,3,5-triazine-2,4,6-trione and 148.5 mg (0.75 mmol) 1,4-butanediol diacrylate were homogenized under an argon atmosphere. 50 mg triethylamine was added as catalyst, and the reaction mixture was stirred at 50° C. for 24 hours. The triethylamine was entrained out by multiple dissolution in dichloromethane. The addition product was obtained as a colourless oil without a perceptible odour. The odour signature did not change even after storage in a refrigerator over a period of 6 months. Gel permeation chromatography tests in tetrahydrofuran as mobile solvent showed, in addition to the still present monomer 1,3,5-tris(3-mercaptopropyl)-1,3,5-triazine-2,4,6-trione (n=0), the dimer (n=1) and trimer (n=2) as main products in addition to a small proportion of higher homologues.

d) Thiol-Michael Addition of tricyclo[5.2.1.0(2.6)]decanedimethyloldiacrylate (TCD-DA) and 1,3,5-tris(3-mercapotopropyl)-1,3,5-triazine-2,4,6-trione

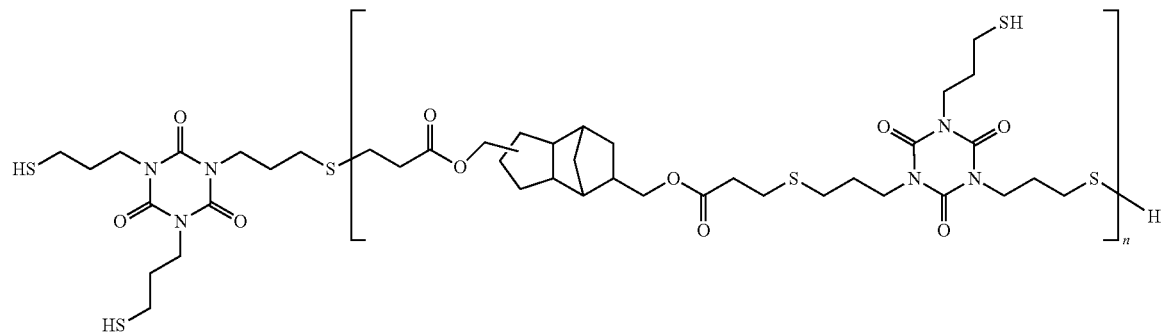

In a 100-mL Schlenk flask, 12.02 g (34.20 mmol) 1,3,5-tris(3-mercaptopropyl)-1,3,5-triazine-2,4,6-trione, 2.60 g (8.55 mmol) tricyclo[5.2.1.0(2.6)]decanedimethyloldiacrylate (TCD-DA) were dissolved in 25 mL tetrahydrofuran. The solution was rinsed thoroughly with nitrogen for 30 min, then 2 mL (1.46 g) triethylamine was added. The reaction solution was stirred at 40° C. for 17 hours and then added to 100 mL of a one molar hydrochloric acid solution. The aqueous phase was extracted three times with dichloromethane. The combined organic phases were then washed with in each case two times 100 mL of a one molar hydrochloric acid solution and a saturated sodium chloride solution, dried over magnesium sulphate, filtered and freed from the solvent on a rotary evaporator under reduced pressure. The addition product was obtained in quantitative yields as an almost odourless, colourless oil, which displayed no change in odour after storage in a refrigerator over a period of 4 months. Gel permeation chromatography tests in tetrahydrofuran as mobile solvent showed, in addition to the still present monomer 1,3,5-tris(3-mercaptopropyl)-1,3,5-triazine-2,4,6-trione (n=0), the dimer (n=1) and trimer (n=2) as main products in addition to a small proportion of higher homologues. (Zero shear viscosity at 25° C.: approx. 113 Pa*s).

Example 4

Filling Composite Based on Thiol-Ene Cross-Linkers

Composite material A and reference A and B (values in mass-%) were prepared according to the Table 1 given below. For this, the reactive components (thiol and ene components) were homogenized together with the stabilizer and the initiator in a Speedmixer centrifugal mixer (from Hauschild) at 1000 RPM for 60 s. The quantity of filler was added to the homogeneous liquid in several portions with decreasing portion size. After each addition, a homogenization took place at 1000 RPM for 60 s in each case. The mixture should become lukewarm but not hot. The final composite paste was achieved after 6-8 additions of filler. A final mixing at 600 RPM for approx. 5 min ensured a bubble-free homogeneous mass.

TABLE 1

Composition of the composite

| Ingredient | Material A | Reference A*) | Reference B*) |
|---|---|---|---|
| TATATO[1] | 10.4 | 12.9 | — |
| Product of Ex. 3d[2] | 21.5 | — | — |
| PETMP[3] | — | 19.0 | — |
| Bis-GMA | — | — | 22.4 |
| TEGDMA | — | — | 9.6 |
| Glass filler G018-053 UF1.5 sil[4] | 67.9 | 67.7 | 67.8 |
| Stabilizer[5] | 0.1 | 0.2 | 0.1 |
| Photoinitiator[6] | 0.1 | 0.3 | 0.1 |
| Total | 100.0 | 100.0 | 100.0 |

*)comparison example
[1]triallyl-1,3,5-triazine-2,4,6-trione
[2]Michael addition of tricyclo[5.2.1.0(2.6)]-decanedimethyloldiacrylate (TCD-DA) and 1,3,5-tris(3-mercaptopropyl)-1,3,5-triazine-2,4,6-trione
[3]pentaerythritol tetrakis (3-mercaptopropionate)
[4]silanized Ba—Al-borosilicate glass filler with an average particle size of 1.5 μm
[5]BHT
[6]radical-forming blue-light-sensitive photoinitiator: TPO Starting from the composite pastes, the test pieces were prepared beginning with carefully filling the respective test piece moulds in several portions, wherein air bubbles were prevented by plugging. The test piece moulds are described in the respective standard tests and the specialist literature. For photopolymerization, the samples were exposed to blue light in the wavelength range around 460 nm. In the examples, dental light devices with a light intensity >850 mW/cm² (Translux Energy model, from Heraeus Kulzer GmbH) were used in order to irradiate the samples in the exposure range for in each case 20 s. The exposure took place on both sides according to the method descriptions in the specialist literature and in EN ISO 4049:2009 (Dentistry-Polymer-based restorative materials).

Compared with the commercially available cross-linker PETMP with the typical mercaptan odour (reference A) and methacrylate-based dental composites (reference B), the composite material A according to the invention displayed much lower shrinkage stress and polymerization shrinkage. The double bond conversions were comparable to the PETMP composite and higher than in the case of methacrylate-based dental composites.

TABLE 2

Properties of the composite

| Material properties | Material A | Reference A*) | Reference B*) |
|---|---|---|---|
| Bending strength [MPa][1] | 110 | 106 | 106 |
| Modulus of elasticity [GPa][2] | 7.7 | 7.4 | 6.3 |
| Double bond conversion [%][3] | 59 | 60 | 48 |
| Polymerization shrinkage [vol.-%][4] | 2.1 | 4.1 | 3.0 |
| Shrinkage stress [MPa][5] | 4.6 | 6.8 | 6.2 |

*)comparison example
[1]according to EN ISO 4049:2009 after 24 h water storage at 37° C.
[2]according to EN ISO 4049:2009 after 24 h water storage at 37° C.
[3]measurement by means of FTIR-ATR after 10 min (20 sec exposure, blue light)
[4]measurement after 10 min ("deflecting disc" method according to Watts & Cash)
[5]measurement after 24 h (photoelastic method according to Ernst)

The invention claimed is:

1. Dental material, which contains at least one thiol and at least one ene compound with two or more C—C multiple bonds, characterized in that it contains at least one thiol according to general Formula (1),

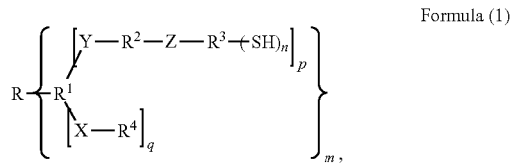

Formula (1)

in which
R is —SO$_2$—, a linear or branched aliphatic C$_{1-20}$ radical, an aromatic C$_{6-20}$ radical, a cycloaliphatic C$_{3-18}$ radical or a heterocyclic radical with 3 to 17 C atoms and 1 to 3 heteroatoms which are selected from N, O and S;
R$^1$ is absent or is a linear or branched aliphatic C$_{1-12}$ radical, an aromatic C$_{6-20}$ radical, a cycloaliphatic C$_{3-18}$ radical or a heterocyclic radical with 3 to 17 C atoms and 1 to 3 heteroatoms which are selected from N, O and S;
R$^2$ is absent or is a linear or branched aliphatic C$_{1-20}$ radical which can be interrupted by O or S, an aromatic C$_{6-10}$ radical which can be substituted by CH$_3$, CH$_2$CH$_3$, OH, OCH$_3$ or —O—CO—CH$_3$;
R$^3$ is absent or is a linear or branched aliphatic C$_{1-20}$ radical which can be interrupted by O or S, an aromatic C$_{6-10}$ radical which can be substituted by CH$_3$, CH$_2$CH$_3$, OH, OCH$_3$ or —O—CO—CH$_3$;
R$^4$ is a C$_{1-6}$ alkyl radical;
X, Y independently of each other are O, S, CO—NH, O—CO—NH or NH—CO—NH or are absent;
Z is O, S, CO—NH, O—CO—NH or NH—CO—NH or is absent;
m is an integer from 1 to 4;
n is an integer from 1 to 4;
p is an integer from 1 to 6;
q is an integer from 0 to 4,
wherein n, p and m are chosen such that the thiol has a total of at least 3 SH groups.

2. Dental material according to claim 1, in which the variables of Formula 1 have the following meanings:
R is —SO$_2$—, a linear or branched aliphatic C$_{1-12}$ radical, an aromatic C$_{6-18}$ radical, a cycloaliphatic C$_{5-8}$ radical or a heterocyclic radical with 3 to 5 C atoms, 1 to 3 heteroatoms and a total of 5-8 ring atoms, wherein the heteroatoms are selected from N, O and S;
R$^1$ is absent, a linear or branched aliphatic C$_{1-10}$ radical or an aromatic C$_{6-10}$ radical;
R$^2$ is absent or is a linear or branched aliphatic C$_{1-10}$ radical or a phenyl radical;
R$^3$ is a linear or branched aliphatic C$_{1-10}$ radical or a phenyl radical;
R$^4$ is a C$_{1-4}$ alkyl radical;
X is O or is absent;
Y is O or is absent;
Z is O or is absent;
m is 1, 2 or 3;
n is 1 or 2;
p is 1, 2 or 3;
q is 0, 1 or 2.

3. Dental material according to claim 2, in which the variables of Formula 1 have the following meanings:
R is —SO$_2$—, a linear or branched aliphatic C$_{1-6}$ radical, an aromatic C$_6$ radical, a cycloaliphatic C$_{5-8}$ radical or a 1,3,5-triazine-2,4,6-trione radical;
R$^1$ is absent, a linear or branched aliphatic C$_{1-6}$ radical or a phenyl radical;
R$^2$ is absent or is a linear or branched aliphatic C$_{1-3}$ radical;
R$^3$ is a linear or branched aliphatic C$_{2-6}$ radical;
R$^4$ is a C$_{1-3}$ alkyl radical;
X is O or is absent;
Y is O or is absent;
Z is O or is absent;
m is 2 or 3;
n is 1;
p is 1 or 2;
q is 0 or 1.

4. Dental material according to claim 3, in which the thiol of general Formula (1) is present as reaction product with a di- or multi-functional acrylate or acrylamide or with a di- or multi-functional isocyanate.

5. Dental material according to claim 4, which contains a vinyl, allyl or norbornene compound or an alkyne as ene compound.

6. Dental material according to claim 5, which contains as ene compound
a vinyl ether, vinyl ester or an N-vinyl amide; and/or
an allyl ether of tri- or higher-functionalized alcohols or a reaction product of tri- or higher-functionalized carboxylic acids with allyl alcohol or allyl amine, a triallyl amine or triallyl-1,3,5-triazine-2,4,6-trione (TATATO);

and/or
an ester of 5-norbornene-2-carboxylic acid with tri- or higher-functionalized alcohols or an ester of 5-norbornene-2-methanol with tri- or higher-functionalized carboxylic acids;
and/or
an ester of propargyl alcohol with tri- or higher-functionalized carboxylic acids or an ether of propargyl alcohol with tri- or higher-functionalized alcohols.

7. Dental material according to claim 6, which additionally contains at least one mono- or multi-functional methacrylate or a mixture thereof.

8. Dental material according to claim 7, which additionally contains an initiator for the radical polymerization.

9. Dental material according to claim 8, which additionally contains organic or inorganic particulate filler.

10. Dental material according to claim 9, which contains the following components:
a) 5 to 40 wt.-% of at least one thiol of general Formula I or an oligomer thereof,
b) 5 to 40 wt.-% of at least one ene component,
c) 0 to 40 wt.-% methacrylate(s),
d) 0.01 to 10 wt.-% initiator(s),
e) 10 to 85 wt.-% filler(s), and
f) 0 to 10 wt.-% additive(s).

11. Dental material according to claim 1 for intraoral use as dental cement, filling composite or veneering material.

12. Process of using the dental material according to claim 1 for preparing an inlay, onlay, crown or bridge comprising forming the inlay, onlay, crown or bridge with the dental material and curing the dental material.

13. Process for preparing an oligomeric thiol, in which a thiol of Formula (I) in a stoichiometric excess is reacted with a di- or multi-functional ene compound or with a di- or multi-functional isocyanate wherein Formula (I) comprises

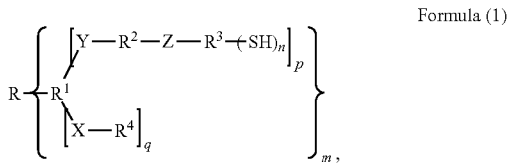

Formula (1)

in which
R is —$SO_2$—, a linear or branched aliphatic $C_{1-20}$ radical, an aromatic $C_{6-20}$ radical, a cycloaliphatic $C_{3-18}$ radical or a heterocyclic radical with 3 to 17 C atoms and 1 to 3 heteroatoms which are selected from N, O and S;
$R^1$ is absent or is a linear or branched aliphatic $C_{1-12}$ radical, an aromatic $C_{6-20}$ radical, a cycloaliphatic $C_{3-18}$ radical or a heterocyclic radical with 3 to 17 C atoms and 1 to 3 heteroatoms which are selected from N, O and S;
$R^2$ is absent or is a linear or branched aliphatic $C_{1-20}$ radical which can be interrupted by O or S, an aromatic $C_{6-10}$ radical which can be substituted by $CH_3$, $CH_2CH_3$, OH, $OCH_3$ or —O—CO—$CH_3$;
$R^3$ is absent or is a linear or branched aliphatic $C_{1-20}$ radical which can be interrupted by O or S, an aromatic $C_{6-10}$ radical which can be substituted by $CH_3$, $CH_2CH_3$, OH, $OCH_3$ or —O—CO—$CH_3$;
$R^4$ is a $C_{1-6}$ alkyl radical;
X, Y independently of each other are O, S, CO—NH, O—CO—NH or NH—CO—NH or are absent;
Z is O, S, CO—NH, O—CO—NH or NH—CO—NH or is absent;
m is an integer from 1 to 4;
n is an integer from 1 to 4;
p is an integer from 1 to 6;
q is an integer from 0 to 4,
wherein n, p and m are chosen such that the thiol has a total of at least 3 SH groups.

14. Process according to claim 13, in which the thiol of Formula (I) is reacted with a di- or multi-functional acrylate, di- or multi-functional acrylamide or di- or multi-functional isocyanate in a molar ratio of SH to acryl or NCO groups of from 1.5:1 to 15:1.

15. Oligomeric thiol, which is obtainable using a process comprising reacting a thiol of Formula (I) in a stoichiometric excess with a di- or multi-functional ene compound or with a di- or multi-functional isocyanate wherein Formula (I) comprises

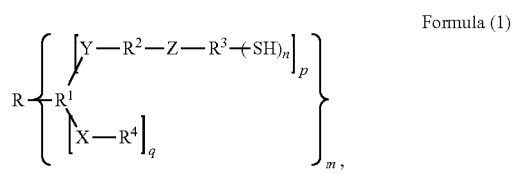

Formula (1)

in which
R is —$SO_2$—, a linear or branched aliphatic $C_{1-20}$ radical, an aromatic $C_{6-20}$ radical, a cycloaliphatic $C_{3-18}$ radical or a heterocyclic radical with 3 to 17 C atoms and 1 to 3 heteroatoms which are selected from N, O and S;
$R^1$ is absent or is a linear or branched aliphatic $C_{1-12}$ radical, an aromatic $C_{6-20}$ radical, a cycloaliphatic $C_{3-18}$ radical or a heterocyclic radical with 3 to 17 C atoms and 1 to 3 heteroatoms which are selected from N, O and S;
$R^2$ is absent or is a linear or branched aliphatic $C_{1-20}$ radical which can be interrupted by O or S, an aromatic $C_{6-10}$ radical which can be substituted by $CH_3$, $CH_2CH_3$, OH, $OCH_3$ or —O—CO—$CH_3$;
$R^3$ is absent or is a linear or branched aliphatic $C_{1-20}$ radical which can be interrupted by O or S, an aromatic $C_{6-10}$ radical which can be substituted by $CH_3$, $CH_2CH_3$, OH, $OCH_3$ or —O—CO—$CH_3$;
$R^4$ is a $C_{1-6}$ alkyl radical;
X, Y independently of each other are O, S, CO—NH, O—CO—NH or NH—CO—NH or are absent;
Z is O, S, CO—NH, O—CO—NH or NH—CO—NH or is absent;
m is an integer from 1 to 4;
n is an integer from 1 to 4;
p is an integer from 1 to 6;
q is an integer from 0 to 4,
wherein n, p and m are chosen such that the thiol has a total of at least 3 SH groups.

16. Dental material according to claim 8, in which the initiator comprises a photoinitiator.

17. Dental material according to claim 9, which contains the following components:
a) 5 to 30 wt.-% of at least one thiol of general Formula I or an oligomer thereof,
b) 5 to 30 wt.-% of at least one ene component,
c) 2 to 30 wt.-% methacrylate(s), d) 0.1 to 3.0 wt.-% initiator(s),
e) 10 to 85 wt.-% filler(s), and
f) 0 to 5 wt.-% additive(s).

18. Dental material according to claim 9, which contains the following components:
  a) 5 to 20 wt.-% of at least one thiol of general Formula I or an oligomer thereof,
  b) 5 to 20 wt.-% of at least one ene component,
  c) 4 to 20 wt.-% methacrylate(s),
  d) 0.1 to 3.0 wt.-% initiator(s),
  e) 10 to 85 wt.-% filler(s), and
  f) 0 to 5 wt.-% additive(s).

19. Process according to claim 14, in which the molar ratio of SH to acryl or NCO groups is from 1.5:1 to 9:1.

* * * * *